United States Patent [19]

Speranza et al.

[11] Patent Number: 4,526,972
[45] Date of Patent: Jul. 2, 1985

[54] ULTRAVIOLET LIGHT STABILIZING STERICALLY HINDERED POLYOXYALKYLENE AMINES

[75] Inventors: George P. Speranza, Austin; Robert A. Grigsby, Jr., Georgetown, both of Tex.

[73] Assignee: Texaco Inc., White Plains, N.Y.

[21] Appl. No.: 624,894

[22] Filed: Jun. 27, 1984

[51] Int. Cl.³ .................. C07D 401/12; C07D 211/58
[52] U.S. Cl. .................... 546/191; 546/186; 524/99; 524/103
[58] Field of Search .............. 546/186, 191; 524/99, 524/103

[56] References Cited

U.S. PATENT DOCUMENTS

| | | | |
|---|---|---|---|
| 3,431,232 | 3/1969 | Murayama | 546/191 |
| 4,014,887 | 3/1977 | Randall et al. | 260/293.84 |
| 4,104,248 | 8/1978 | Cantatore | 546/186 |
| 4,366,277 | 12/1982 | Molt | 524/102 |
| 4,369,275 | 1/1983 | Rody | 524/103 |
| 4,377,690 | 3/1983 | Moser | 546/191 |
| 4,382,109 | 5/1983 | Olson et al. | 428/331 |
| 4,386,127 | 5/1983 | Tanaka et al. | 428/91 |
| 4,415,688 | 11/1983 | Minagawa et al. | 546/186 |

FOREIGN PATENT DOCUMENTS 0070386  8/1982  European Pat. Off. .

OTHER PUBLICATIONS

"Sterically Hindered Amines and Nitroxyls as Polymer Stabilizers", Dagonneau, Ivanov, Rozantsev, Sholle & Kagan (Lab. Rech. Macromol. Sci. Rev. Macromol. Chem. Phys., 1982, C22(2), 169–202 (Eng.).

"Light Stabilization of Polyurethanes", K. Berger, Kunstat. Fortschrittake, 1980, 7, 80–94.

Primary Examiner—Paul R. Michl
Assistant Examiner—A. H. Walker
Attorney, Agent, or Firm—Jack H. Park; Kenneth R. Priem

[57] ABSTRACT

This invention relates to ultraviolet light stabilizing hindered polyoxyalkylene polyamines. The products of the present invention can be utilized as ultraviolet light stabilizers for a wide variety of commercial products such as water base paints, oil base paints, polyethylenes, polypropylenes, polyurethanes, etc. The products have the formula:

$$R-\left[(OCH_2CH)_n-N-\underset{H}{\underset{|}{C}}-\underset{}{\underset{}{}}N-H\right]_x \quad (I)$$

wherein:
R represents an alkylene, alkyl, aralkyl, alkaryl or aryl group containing 1 to 24 carbon atoms,
R' represents hydrogen, methyl or ethyl,
n represents a number having an average value of 1 to 70, and
x represents an integer having a value of 1 to 3.

In a modified form of the invention, the products are useful also to inhibit oxidation of such products. The compounds have the formula:

$$(II)$$

wherein: the letters and subscripts of formula (II) have the same meaning as the letters and subscripts of formula (I), except that x equals 1 or 2 and R" represents an alkylene group or:

$$CH_3CH_2\underset{\underset{C-CH_2}{|}}{\overset{\overset{CH_2-}{|}}{C}}-CH_2-$$

and when x = 1, W equals $-CH_2-\!\!\bigcirc\!\!-OH$, and when x = 2, W equals H, or $-\!\!\!\bigtriangleup\!\!\!-N$, or $-CH_2-\!\!\bigcirc\!\!-OH$ 20 Claims, No Drawings

ULTRAVIOLET LIGHT STABILIZING STERICALLY HINDERED POLYOXYALKYLENE AMINES

BACKGROUND OF THE INVENTION

1. Technical Field of the Invention

This invention relates to ultraviolet light stabilizing sterically hindered polyoxyalkylene polyamines. In another aspect this invention relates to ultraviolet light stabilizing; oxidation inhibiting hindered polyoxyalkylene polyamines. In yet another aspect, the present invention is directed to the preparation of compounds of the type mentioned above by reacting a 2,2,6,6-tetramethyl-4-piperidone with a polyoxyalkylene polyamine under Schiff base reaction conditions to form a Schiff base which is thereafter hydrogenated to form the desired ultraviolet light stabilized hindered polyoxyalkylene polyamine. In a modified form of the present invention a polyoxyalkylene polyamine is reacted with 2,2,6,6-tetramethyl-4-piperidone and hydrogenated to form the sterically hindered polyamine, which is then reacted with a hindered phenol such as 2,6-ditertiarybutylphenol and formaldehyde under Mannich condensate reaction conditions to form a Mannich derivative containing a sterically hindering oxidation inhibiting group. The products of the present invention can be utilized as ultraviolet light stabilizers for a wide variety of commercial products such as water base paints, oil base paints, polyethylenes, polypropylenes, polyurethanes, etc. In the modified form of the invention, the products are useful also to inhibit oxidation of such products.

By way of summary, the 2,2,6,6-tetramethyl-4-piperidone when reacted with the polyoxyalkylene polyamine under Schiff base reaction conditions will provide a product which, when hydrogenated will have the formula:

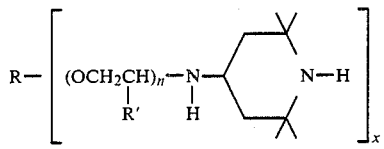

wherein:

R represents an alkylene, alkyl, aralkyl, alkaryl, or aryl group containing 1 to 24 carbon atoms, R' represents hydrogen, methyl or ethyl, n represents a number having an average value of 1 to 70, and x represents an integer having a value of 1 to 3.

In accordance with the modified form of the present invention wherein the product of formula I is reacted with a hindered phenol and formaldehyde under Mannich condensate reaction conditions, the Mannich derivate may be represented by the formula:

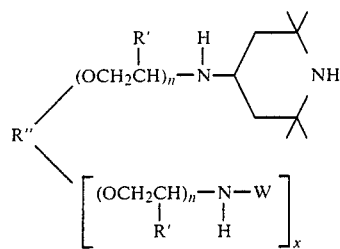

wherein: the letters and subscripts of formula (II) have the same meaning as the letters and subscripts of formula (I), except that x equals 1 or 2 and R" represents an alkylene group or:

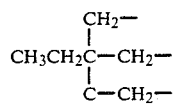

and:

when x = 1, W = 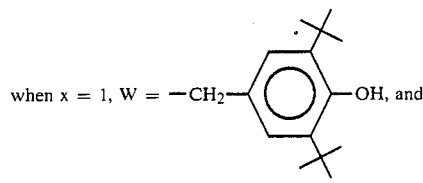 OH, and when x = 2, W equals H, or 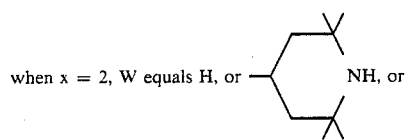 NH, or

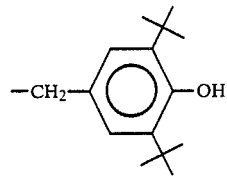 OH

2. Prior Art

It is known to use hindered compounds such as 2,2,6,6-tetramethyl-4-piperidone and derivatives thereof as ultraviolet light stabilizers. See, for example the review entitled "Sterically Hindered Amines and Nitroxyls as Polymer Stabilizers," Dagonneau, Ivanov, Rozantsev, Sholle and Kagan (Lab. Rech. Macromol., Univ. Paris-Nord, 93430 Villetaneuse, Fr.) J. Macromol. Sci. Rev. Macromol. Chem. Phys., 1982, C22(2), 169–202 (Eng.).

European patent application No. 0070386 for Loffeiman filed Aug. 6, 1982 discloses the preparation and use of piperidinyl analogs as ultraviolet light stabilizers. Similarly, dimeric piperidinyl derivative dimers are shown for use as light stabilizers in an article entitled "Light Stabilization of Polyurethanes", K. Berger, *Kunstat. Fortschrittake* 1980, 7, 80–94.

In the United States, U.S. Pat. No. 4,369,275 for Rody discloses Malonate derivatives of sterically hindered piperidinyl compounds as ultraviolet light stabilizers.

Molt U.S. Pat. No. 4,366,277 discloses compounds having 2-bis(2,2,6,6-tetramethyl-4-piperidyl) substituted heterocyclic rings and polymers containing the same which are shown to be useful as ultraviolet light stabilizers. Other U.S. patents of this gender include Tanaka et al. U.S. Pat. No. 4,386,127, Olson et al. U.S. Pat. No. 4,382,109 and Randall et al. U.S. Pat. No. 4,014,887.

SUMMARY OF THE INVENTION

In one aspect the present invention is directed to ultraviolet light stabilizing sterically hindered polyoxyalkylene polyamines. In another aspect of the present invention, polyoxyalkylene polyamine products are provided containing one or more ultraviolet stabilizing sterically hindered groups and one or more oxidation inhibiting sterically hindered groups.

The products can be used for the stabilization of a wide variety of materials such as surface coatings, olefin polymers such as polyethylene and polypropylene, for polyurethanes, etc. The products of the present invention can be prepared as either water soluble products or oil soluble products, depending upon the chemical identity of the polyoxyalkylene polyamine starting material.

The light stabilizing products are prepared by reacting 2,2,6,6-tetramethyl-4-piperidone with the polyoxyalkylene polyamine starting material under Schiff base forming conditions such as a temperature within the range of about 40° to about 200° C., a reaction time of about 1 to about 24 hours and, preferably, ambient pressures. The product formed by this reaction, a Schiff base, can then be recovered and hydrogenated under conventional hydrogenation conditions (e.g., in the presence of a hydrogenation catalyst such as a nickel, cobalt, nickel and copper or cobalt and copper or nickel-copper, chromia hydrogenation catalysts, a noble metal hydrogenation catalyst, etc. under hydrogenation conditions including a temperature within the range of about 40° to about 200° C., and more preferably 80° to about 200° C. and a pressure of about 50 to about 5000 psig., and more preferably from about 1000 to about 3000 psig. From about 1 to about 15 moles of hydrogen per mole of substituted piperidone should be employed.

When it is desired to incorporate an oxidation inhibiting group into a polyamine product, a piperidone reaction product containing one or more primary amine groups is reacted with a sterically hindered phenol and formaldehyde under Mannich condensate reaction conditions.

DETAILED DESCRIPTION

The principle components from which the products of the present invention are made and by which the methods of the present invention are practiced are a polyoxyalkylene polyamine, a sterically hindered phenol and 2,2,6,6-tetramethyl-4-piperidone.

2,2,6,6-Tetramethyl-4-piperidone can be structurally represented by the following formula III or graphically represented by graphic formula IV.

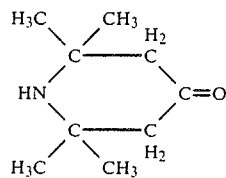   (III)

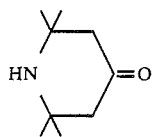   (IV)

The sterically hindered phenol, such as 2,6-ditertiarybutylphenol, can be represented structurally by structural formula V given below, or graphically by graphic formula VI.

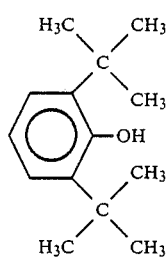   (V)

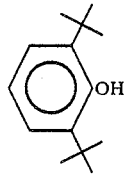   (VI)

The Polyoxyalkylene Polyamine Starting Material

The polyoxyalkylene polyamine starting material may be structurally represented by one or more of the following formulae:

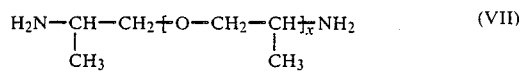   (VII)

wherein x has an average value of from about 2 to about 70.

Representative products having this structural formula include a product having a molecular weight of 230 wherein x has a value between about 2 and 3, a product having an average molecular weight of about 400 wherein x has a value between about 5 and 6, a product having a molecular weight of about 2000 wherein x has a value of about 33, and a product having a molecular weight of about 4000 where x has a value of about 60.

Another class of polyoxyalkylene polyamines that may be used in accordance with the present invention are those having formula VIII given below:

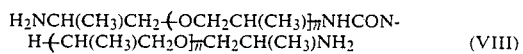   (VIII)

wherein n has a value of about 2 to about 60.

Representative products having this formula include a commercial product having an average molecular weight of about 820 containing 1 urea group, a product having a molecular weight of about 1700 containing about 3 moles of urea and a product having a molecular weight of about 3000 containing about 1 mole of urea.

Another class of polyoxalkylene polyamines that may be used as starting materials for the present invention are those having formula IX given below:

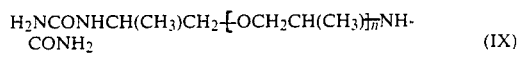

wherein n has a value of about 2 to about 60.

An example of such a product is a commercial product having a molecular weight of about 2000 wherein n has a value of about 33.

Yet another example of a class of polyoxyalkylene polyamines useful as raw materials in accordance with the present invention are those having formula X given below:

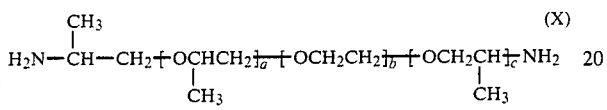

wherein a+c equals 2 to 10 and b is a number having a value of from about 1 to about 50.

Examples of products having this general formula include a commercial product having an average molecular weight of about 600 wherein the value of b is about 8.5 and the value of a+c is about 2.5, a product having an average molecular weight of about 900 wherein the value of a+c is again 2.5 and the value of b is about 15.5. Other examples wherein a+c has a value of about 2.5 include a product having an average molecular weight of about 2000 wherein the value of b is about 40 and a product having a molecular weight of about 4000 wherein the value of b is about 85.

A further example of suitable products for use in accordance witht the present invention are those having the formula XI given below:

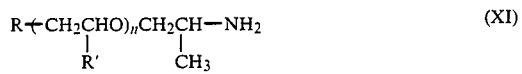

R' = H—, CH$_3$—, C$_2$H$_5$

R=C$_{1-12}$ alkoxy or C$_1$-C$_{12}$ alkoxyethoxy and n has a value of about 2 to 40.

Examples of such products include a product having a molecular weight of about 300 wherein R' is methyl, and R represents an alkoxy C$_{10-12}$ group; a commercial product having an average molecular weight of about 360 where R represents a normal butoxy group and R' is hydrogen and methyl, with a ratio of methyl to hydrogen of about 2 to 3; a product having an average molecular weight of 600 wherein R is methoxyethoxy, R' is methyl and n has a value of about 9; a product having an average molecular weight of about 1000 wherein R is methoxyethoxy, R' is sometimes hydrogen and sometimes methyl with a ratio of methyl to hydrogen of 3 to 18; a product having an average molecular weight of about 2000 wherein R is methoxyethoxy, wherein R' is primarily H with a ratio of H to methyl of about 32 to 2; and a product having the molecular weight of about 2000 wherein R is methoxyethoxy, R' is sometimes H and sometimes methyl with a ratio of hydrogen to methyl of 10 to 31. The alkoxy amines described above are available from Texaco Chemical Company.

A still further example of a class of polyoxyalkylenepolyamine starring material for use in accordance with the present invention are those having formula XIII given below:

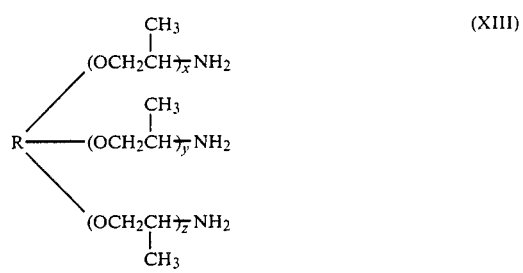

wherein

R represents the use of a trifunctional alkyl group such as trimethylolpropane, glycerine, trimethylolethane, etc.

x, y and z are numbers, and the sum of x+y+z is about 5 to about 90.

Formation of the Ultraviolet Light Stabilizing Sterically Hindered Polyoxalkylene Amine When the product that is desired is an ultraviolet light stabilizing sterically hindered polyoxyalkylene polyamine, such as a diamine, two moles of 2,2,6,6-tetramethyl-4-piperidone may be reacted with the diamine under Schiff base reaction conditions in organic solvent solution as illustrated by the following equation:

(IV)

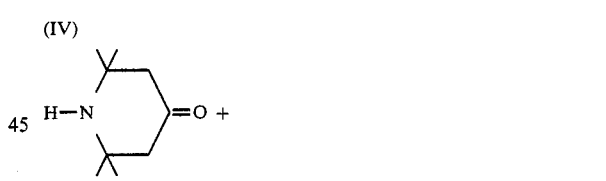

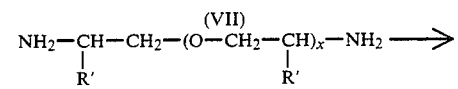

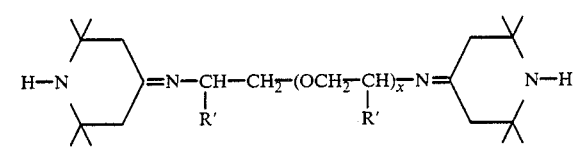

(XII)

R' = H, CH$_3$, C$_2$H$_5$
x = 2~50

The thus formed Schiff base is then hydrogenated under conventional hydrogenation conditions to form the corresponding bis-piperidine compound illustrated, for example, by formula XIV given below:

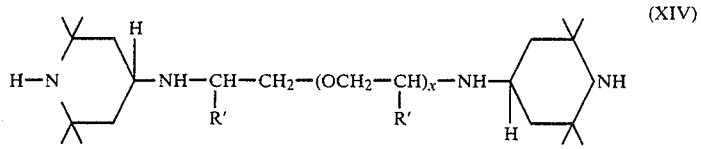

The hydrogenation conditions to be employed are those conventionally employed for hydrogenation reactions of this general nature using a hydrogenation catalyst such as a noble metal, a nickel or cobalt catalyst, a nickel-copper-chromia catalyst, etc. Hydrogenation conditions may suitably include a temperature within the range of about 40° to about 200° C. and a pressure within the range of about 50 to about 5000 psig. Higher pressures may be utilized if desired, but there is no particular advantage in doing so. A preferred temperature range is about 80° to about 200° C. and a preferred pressure range is from about 1000 to about 3000 psig.

If less than a molar equivalent amount of the 2,2,6,6-tetramethyl-4-piperidone is used, based on the primary amine groups, the sterically hindered product will contain free primary amine groups. These unreacted amine groups can be used as reaction sites for the addition, for example, of an oxidation inhibitor in a manner to be described, or as reactive sites for incorporating the sterically hindered polyoxyalkylene polyamine into a polymer such as a polyurethane.

By way of illustration of this embodiment of the present invention, about a one-third molar equivalent of 2,2,6,6-tetramethyl-4-piperidone may be reacted with a polyoxyalkylene triamine to form the corresponding Schiff base as illustrated by the equation given below:

To a 500-ml. 3-neck flask equipped with a stirrer, thermometer, K-head and condenser was added 50 grams of 2,2,6,6-tetramethyl-4-piperidone (0.322 moles), 100 g of cyclohexane and 96.8 g (0.16moles) of polyoxyalkylene polyamine Jeffamine ED-600 amine. The mixture was heated to 87°–93° C. for four hours. When a two phase system remained the cyclohexane was distilled and xylene added. The mixture was heated for seven hours with xylene boiling at 147°–150° C. The xylene was removed and 137.5 g of product obtained. The NMR showed C=N present with no starting material. This product was hydrogenated as shown in Table 1 (5788-24). Table 1 names the reactants used to make the amine. For example in 5788-28, 35.8 grams of triethyleneglycoldiamine (TGD) were allowed to react with 75 grams of 2,2,6,6-tetramethylpiperidone in boiling toluene (toluene and xylene were used to azeotrope water to make the diamine). After the toluene was distilled a small amount of the imine was taken for analysis and the rest was added to 300 grams of methanol. The imine was hydrogenated over a reduced cobalt-copper-chrome catalyst with 78 grams of ammonia at 2000 psig and 140° C.

The reaction products were analyzed for structure by NMR.

Attached Table 1 gives information for ultraviolet

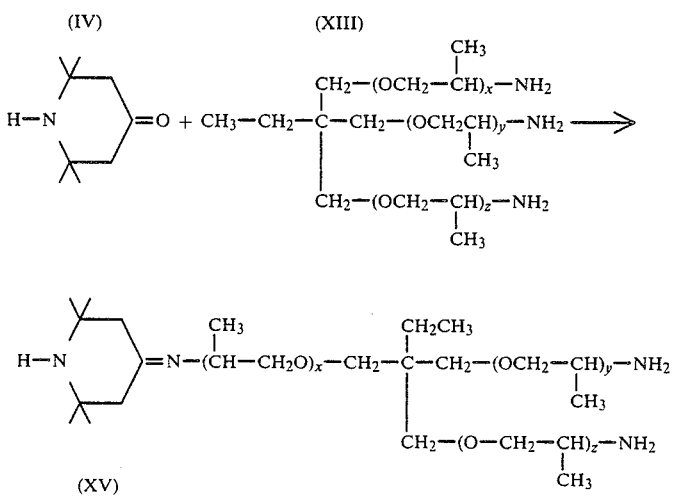

$x + y + z = 5$ to about 90

This material, after hydrogenation, may then be reacted with a hindered phenol, if desired, such as 2,6-ditertiarybutylphenol and formaldehyde under Mannich base forming conditions to form the corresponding Mannich base.

SPECIFIC EXAMPLES

In preparing the products which are summarized in Table 1, the following reaction procedure was utilized for each experiment:

light stabilizing sterically hindered polyoxyalkylene polyamines while Table 2 gives the results obtained when the sterically hindered polyamine was further reacted with 2,6-ditertiarybutylphenol and formaldehyde to form a Mannich condensate.

The compounds that are identified in Table 1 and Table 2 were found to have the structural formulae given in Chart 1.

TABLE 1

| | \multicolumn{11}{c}{Reactions of 2,2,6,6-Tetramethyl-4-Piperidone} | | | | | | | | | | |
|---|---|---|---|---|---|---|---|---|---|---|---|
| | 5788-24 | 5788-28 | 5788-99 | 5812-01 | 5812-07 | 5812-08 | 5812-57 | 5812-73 | 5812-74 | 5812-77 | 5812-78 |
| Jeffamine | | | | | | | | | | | |
| Amine | ED-600[1] | TGD[2] | D-400[3] | D-230[4] | ED-600 | T-403[5] | TGD | ED-900[6] | ED-900 | M-1000[7] | M-600[8] |
| Grams | 96.8 | 35.8 | 193.5 | 148.4 | 193.5 | 208 | 162.5 | 290.3 | 290.3 | 190.0 | 114.0 |
| Moles | 0.16 | 0.24 | 0.48 | 0.645 | 0.32 | 0.52 | 1.06 | 0.32 | 0.32 | 0.19 | 0.19 |
| 2,2,6,6-TMP-4[9] | | | | | | | | | | | |
| Grams | 50.0 | 75.0 | 75 | 100 | 50 | 80 | 169.5 | 100 | 50 | 30 | 30 |
| Moles | 0.32 | 0.48 | 0.48 | 0.645 | 0.32 | 0.52 | 1.06 | 0.64 | 0.32 | 0.19 | 0.19 |
| Solvent | MEOH | MEOH | MEOH | MEOH | MEOH | MEOH | MEOH | MEOH | MEOH | MEOH | MEOH |
| Grams | 300 | 300 | 250 | 250 | 250 | 250 | 200 | 300 | 300 | 300 | 300 |
| $NH_3$, grams | 55 | 78 | — | — | 57.1 | 93.4 | 160 | — | 55 | — | — |
| Hydrogen (psi) | 2000 | 2000 | 2000 | 2000 | 2000 | 2000 | 2000 | 2000 | 2000 | 2000 | 2000 |
| Cobalt-1006 (g) | 15.0 | 15.0 | 24 | 22 | 25 | 30 | 25 | 36 | 32 | 21.0 | 13 |
| Temp. (C) | 140 | 140 | 140 | 140 | 140 | 140 | 140 | 140 | 140 | 140 | 140 |
| Total amines, meq/g | 4.51 | 12.7 | 4.85 | 7.55 | 3.37 | 6.24 | 10.3 | 2.72 | 3.18 | 1.20 | 2.18 |
| NMR | Good | Good | Good | Good | Good | Good | Good | Good | Good | Good | Good |
| Water Sol. | Yes Hazy | Yes | Yes | No | Yes | No | Yes | Yes | Yes | Yes | No |

Footnotes - See Chart 1

TABLE 2

| \multicolumn{7}{c}{Mannich Reaction of Piperidone Derivative with 2,6-Ditertbutylphenol and Formaldehyde} | | | | | | |
|---|---|---|---|---|---|---|
| | 5812-53 | 5812-61 | 5812-62 | 5812-93 | 5812-94 | 5812-95 |
| Amine from Table 1 | 5812-08 | 5812-07 | 5788-99 | 5812-01 | 5812-57 | 5812-74 |
| Grams | 100 | 100 | 100 | 75 | 75 | 75 |
| Moles | 0.185 | 0.135 | 0.186 | 0.2 | 0.25 | 0.07 |
| 2,6 Di T-Butyl Phenol (g) | 76.3 | 27.8 | 38.2 | 40.1 | 51.1 | 14.6 |
| Moles | 0.37 | 0.135 | 0.186 | 0.2 | 0.25 | 0.07 |
| Formalin Moles | 0.37 | 0.135 | 0.186 | 0.2 | 0.25 | 0.07 |
| Temp. °C. | 90 | 90 | 90 | 90 | 90 | 90 |
| Hours | 8 | 8 | 8 | 8 | 6 | 8 |
| Total Amine, meq/g. | 3.47 | 2.56 | 3.45 | 4.79 | 5.66 | 2.48 |
| Hydroxyl number | | | | 248 | 280 | 124 |
| Water Sol. | No | No | No | No | No | Yes Hazy |

CHART 1

Footnotes for Table 1

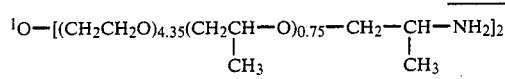  (XXV)

[2]$NH_2CH_2CH_2OCH_2CH_2OCH_2CH_2NH_2$  (XXVI)

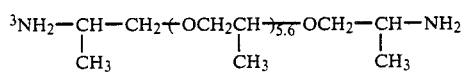  (XXVII)

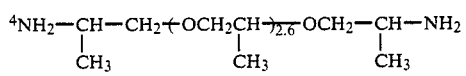  (XXVIII)

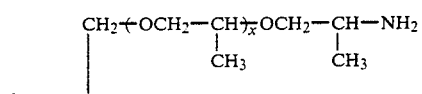  (XXIX)

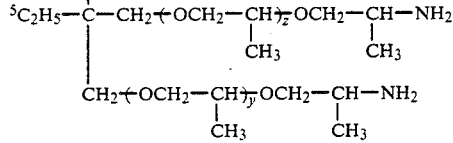

$x + y + z = 5.3$

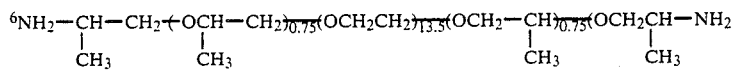  (XXX)

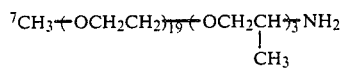  (XXXI)

-continued
CHART 1
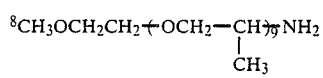 (XXXII)
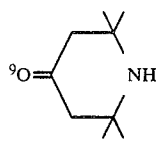 (XXXIII)
Product Structures
Number 5812-53
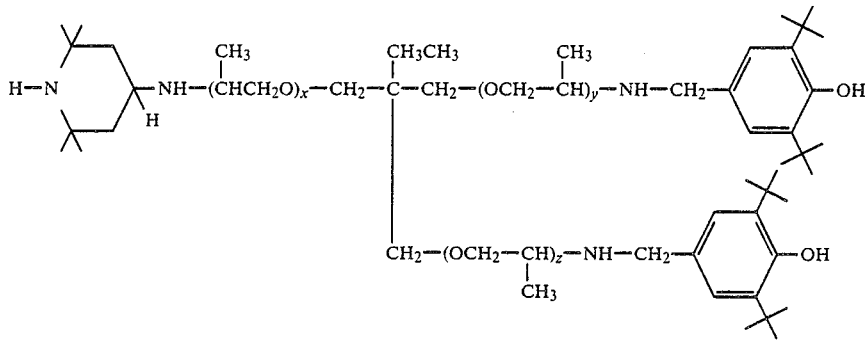 (XXV)
x + y + z = 5.3
Number 5812-61
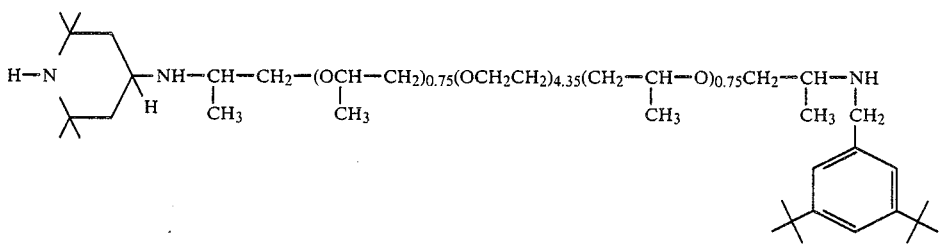 (XXVI)
Number 5812-62
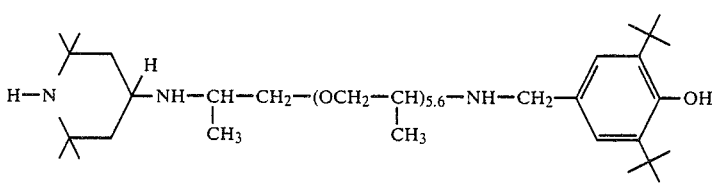 (XXVII)
Number 5812-93
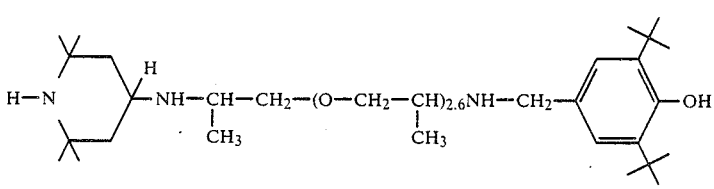 (XXVII)
Number 5812-94
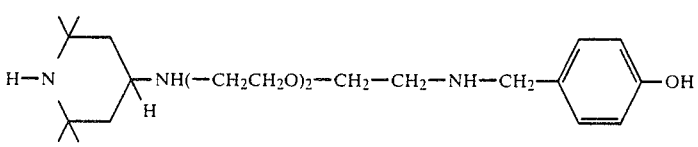 (XXVIII)
Number 5812-95

-continued
CHART 1

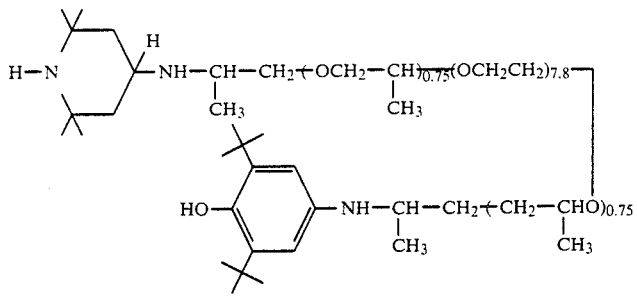
(XXIX)

As will be seen from Table 1, a variety of products were obtained, some of which were water soluble and some of which were oil soluble.

Table 2 shows the products obtained which were essentially water insoluble.

Having thus described our invention, what is claimed is:

1. A compound having the formula:

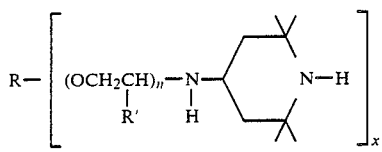
(I)

wherein:
R represents an alkylene, alkyl, aralkyl, alkaryl or aryl group containing 1 to 24 carbon atoms,
R' represents hydrogen, methyl or ethyl,
n represents a number having an average value of 1 to 70, and
x represents an integer having a value of 1 to 3.

2. A compound as in claim 1 having the formula:

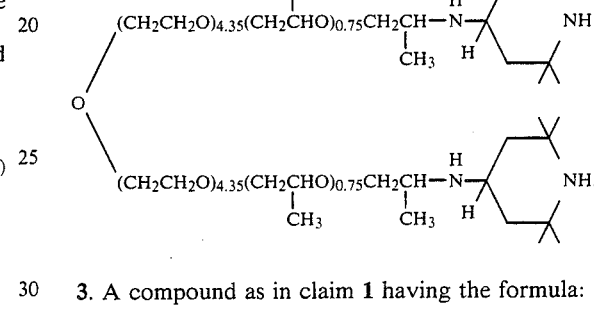

3. A compound as in claim 1 having the formula:

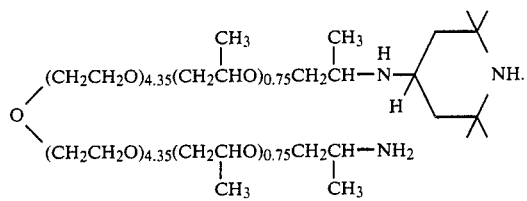

4. A compound as in claim 1 having the formula:

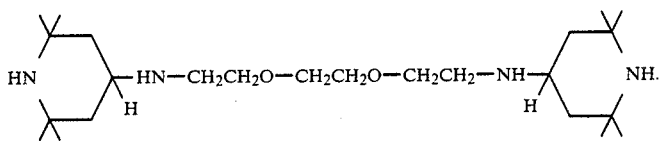

5. A compound as in claim 1 having the formula:

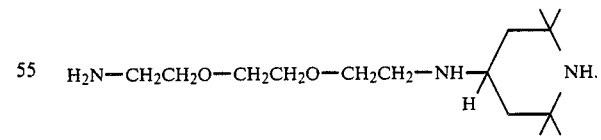

6. A compound as in claim 1 having the formula:

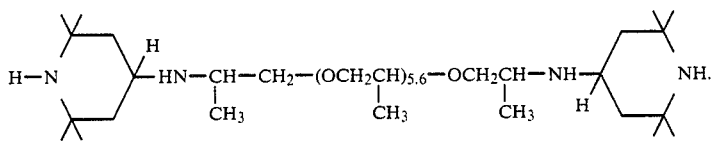

7. A compound as in claim 1 having the formula:

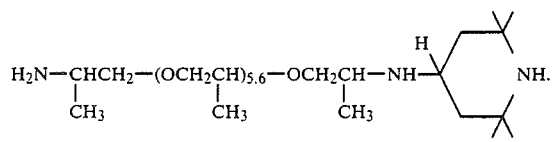

8. A compound as in claim 1 having the formula:

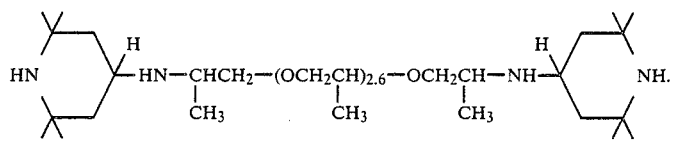

9. A compound as in claim 1 having the formula:

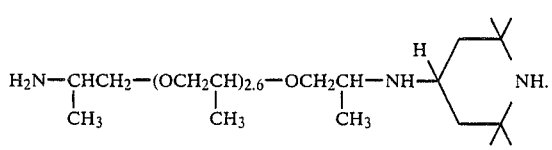

10. A compound as in claim 1 having the formula:

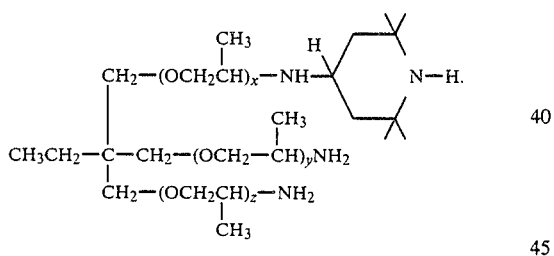

11. A compound as in claim 1 having the formula:

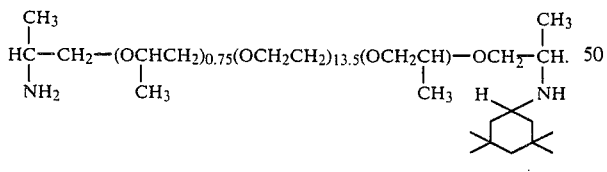

12. A Mannich condensate derivative of formaldehyde, a ditertiary butyl phenol and a compound having the formula:

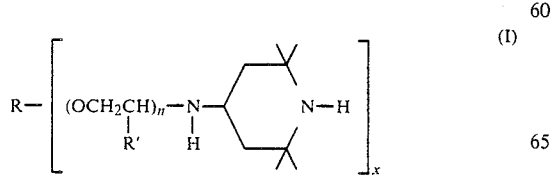

(I)

wherein:

R represents an alkylene, alkyl, aralkyl, alkaryl or aryl group containing 1 to 24 carbon atoms, R' represents hydrogen, methyl or ethyl, n represents a number having an average value of 1 to 70, and x represents an integer having a value of 1 to 3;

said Mannich condensate derivative having the following formula:

(II)

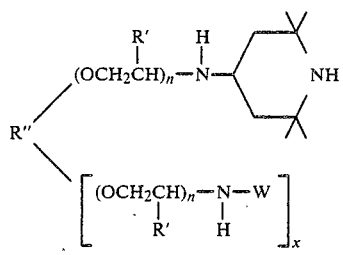

wherein:

the letters and subscripts of formula (II) have the same meaning as the letters and subscripts of formula (I), except that x has a value of 1 to 2, and:

R" represents an alkylene group or

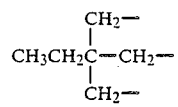

and:

when x = 1, W equals 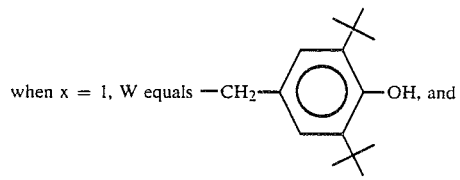, and when x = 2, W equals H, or 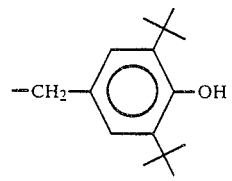 or

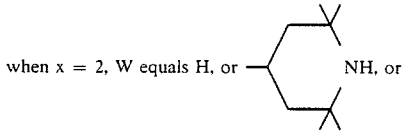

13. A compound as in claim 12 having the formula:

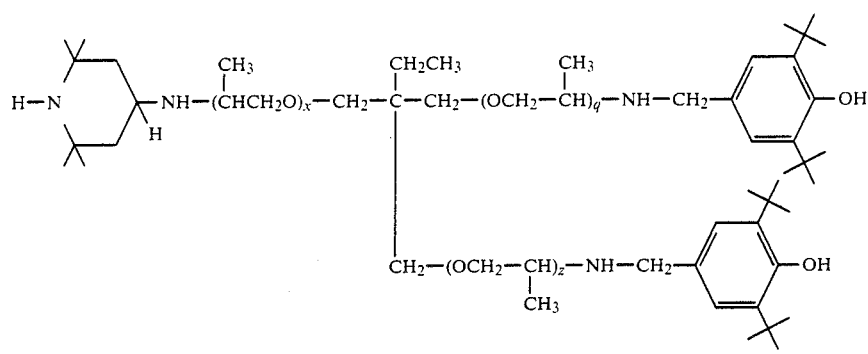
(XXV)
14. A compound as in claim 12 having the formula:
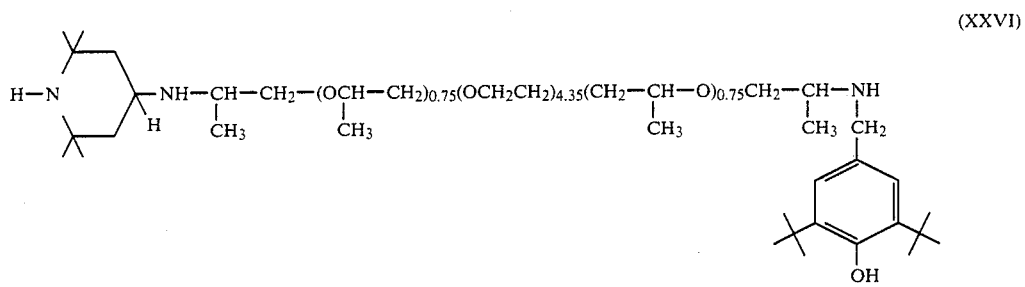
(XXVI)
15. A compound as in claim 12 having the formula:
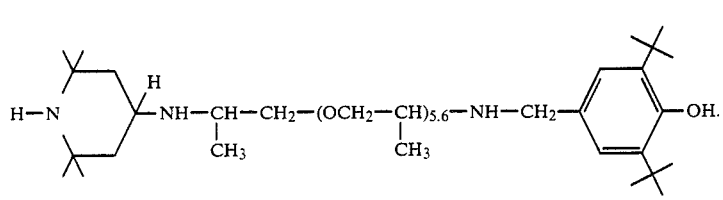
(XXVII)
16. A compound as in claim 12 having the formula:
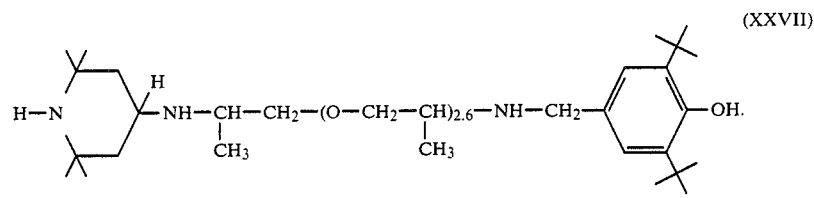
(XXVII)
17. A compound as in claim 12 having the formula:
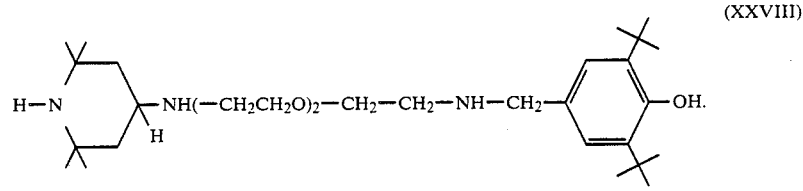
(XXVIII)
18. A compound as in claim 12 having the formula:

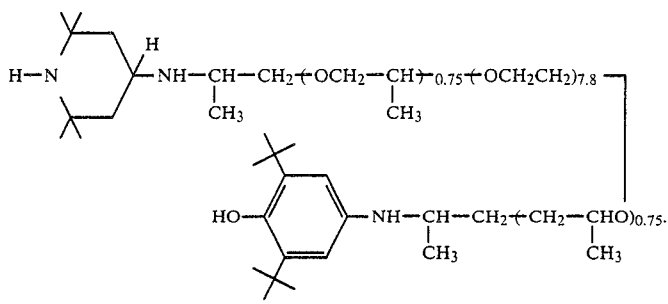
(XXIX)

19. A method which comprises reacting at least one molar equivalent of 2,2,6,6-tetramethyl-4-piperidone under Schiff base raction conditions with an amine having the formula:

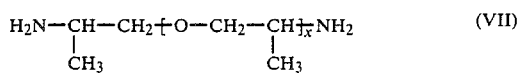
(VII)

wherein x has an average value of from about 2 to about 60 and thereafter hydrogenating the resultant Schiff base product to thereby provide a light stabilizing sterically hindered polyoxyalkylenepolyamine.

20. A method as in claim 19 wherein the 2,2,6,6-tetramethyl-4-piperidone is reacted with one molar equivalent of the amine and wherein the hydrogenated Schiff base product is further reacted with 2,6-ditertbutylphenol and formaldehyde under Mannich base reaction conditions to thereby provide an oxidation inhibiting, light stabilizing sterically hindered polyoxyalkylenepolyamine.

* * * * *